United States Patent
Lee et al.

(10) Patent No.: US 12,226,073 B2
(45) Date of Patent: Feb. 18, 2025

(54) ENDOSCOPE HAVING POWER ACCOMMODATION UNIT

(71) Applicant: MEDINTECH INC., Seoul (KR)

(72) Inventors: Chi Won Lee, Namyangju-si (KR); Myung Joon Kim, Gwacheon-si (KR); Suk Gyu Koh, Seoul (KR)

(73) Assignee: MEDINTECH INC., Seoul (KR)

( * ) Notice: Subject to any disclaimer, the term of this patent is extended or adjusted under 35 U.S.C. 154(b) by 0 days.

(21) Appl. No.: 18/288,184

(22) PCT Filed: Dec. 2, 2022

(86) PCT No.: PCT/KR2022/019499
§ 371 (c)(1),
(2) Date: May 6, 2024

(87) PCT Pub. No.: WO2023/106747
PCT Pub. Date: Jun. 15, 2023

(65) Prior Publication Data
US 2024/0324851 A1 Oct. 3, 2024

(30) Foreign Application Priority Data
Dec. 8, 2021 (KR) .................. 10-2021-0174879

(51) Int. Cl.
*A61B 1/00* (2006.01)
*A61B 1/005* (2006.01)
(52) U.S. Cl.
CPC ...... *A61B 1/00029* (2013.01); *A61B 1/00114* (2013.01); *A61B 1/00124* (2013.01); *A61B 1/0057* (2013.01)

(58) Field of Classification Search
CPC ............ A61B 1/00029; A61B 1/00114; A61B 1/00124; A61B 1/0057; A61B 1/00105; A61B 1/0051
See application file for complete search history.

(56) References Cited

U.S. PATENT DOCUMENTS

| 4,919,112 A | * | 4/1990 | Siegmund ............ A61B 1/0052 |
| | | | 600/146 |
| 2009/0287043 A1 | * | 11/2009 | Naito ..................... A61B 34/70 |
| | | | 600/104 |

(Continued)

FOREIGN PATENT DOCUMENTS

| JP | 05-329097 A | 12/1993 |
| JP | 2002-325724 A | 11/2002 |

(Continued)

OTHER PUBLICATIONS

International Search Report for PCT/KR2022/019499 mailed Mar. 9, 2023 from Korean Intellectual Property Office.

*Primary Examiner* — Aaron B Fairchild
(74) *Attorney, Agent, or Firm* — Revolution IP, PLLC

(57) ABSTRACT

The present invention relates to an endoscope including a connector configured to be coupled to an external device and receive power from the external device, wherein the connector includes: a power transmission cable configured to transmit power to a bendable section; a power receiving part comprising a first slider configured to move in a first direction by receiving power from the external device and a second slider configured to move in a second direction by receiving power from the external device like the first slider; and a power transmission part configured to receive power from the power receiving part and transmit the same to the power transmission cable.

8 Claims, 7 Drawing Sheets

(56) References Cited

U.S. PATENT DOCUMENTS

| | | |
|---|---|---|
| 2015/0080658 A1 | 3/2015 | Chung et al. |
| 2015/0112143 A1* | 4/2015 | Ando ................... A61B 1/0052 600/149 |
| 2021/0113068 A1 | 4/2021 | Shin et al. |

FOREIGN PATENT DOCUMENTS

| | | |
|---|---|---|
| KR | 10-2012-0014831 A | 2/2012 |
| KR | 10-2015-0030949 A | 3/2015 |
| KR | 10-2019-0121497 A | 10/2019 |

* cited by examiner

ENDOSCOPE HAVING POWER ACCOMMODATION UNIT

TECHNICAL FIELD

The present disclosure relates to an endoscope having a power receiving part and, more particularly, to an endoscope including a power receiving part configured to receive power from a light source device in order to bend a bendable section.

BACKGROUND ART

The information disclosed in this section is only provided for an understanding of background information of embodiments of the present disclosure and should not be taken as a description of the prior art.

An endoscope generally refers to a medical instrument for examining the interior of the body for medical purposes. Such an endoscope may be referred to as a "bronchoscope," a "gastric endoscope," a "laparoscope," or a "colonoscope" depending on the area to be examined therewith. Unlike most medical imaging devices, the endoscope is a medical device which is inserted directly into the body.

Due to the development of optical fibers and the rapid development of optical technology and electronics, endoscope technology has reached the stage of the current electronic endoscope and has made a great contribution to the development of the field of gastroenterology. With the development of the electronic endoscope, the electronic endoscope is used not only in the diagnostic field to directly look into and perform histological examinations of a subject's body, but may also replace invasive surgery due to the rapid development of various treatment endoscopes.

The configuration of the endoscope may generally include an insertion tube configured to be inserted into the patient's body with a bendable section and a flexible portion, a control body connected to one end of the insertion tube to control the bending motion of the bendable section, a connector coupled to a light source device, or the like, and a universal code spacing the control body and the connector apart from each other.

The endoscope has a structure in which a mechanical cord (or cable) is disposed between the bendable section and the control body to control the bending motion of the bendable section and the mechanical cord is connected to a control knob disposed on the control body. According to the structure of the endoscope, when the user, a doctor, manually operates the control knob, the mechanical cord transmits power to enable the bending motion of the bendable section.

While a doctor is performing an endoscopy, an emergency situation fatal to the patient may occur. However, such an endoscope having the above-described structure requires a doctor to control the bending motion of the bendable section by manually operating the knob in the emergency situation, thereby causing the doctor to only focus on operating the knob. Thus, it may be difficult to overcome the emergency situation, and the bending motion of the bendable section may not be accurately performed.

Therefore, there was developed an endoscope in which the bending motion of a bendable section may be performed automatically using a power source rather than by a manual operation of a doctor. However, the endoscope with this structure may have control precision and stability problems due to the absence of an appropriate power transmission structure able to receive power from the outside of the endoscope.

Therefore, there is an urgent need to develop a connector having a novel structure by which the endoscope may receive power from an external source and efficiently transmit the same to the bendable section while maintaining precision in the control of the bending angle of the bendable section.

In addition, the connector of the endoscope and a connector receptacle of an external device such as a light source device are required to be physically coupled to each other so that the endoscope can receive power from the external device. Thus, the connector may be subjected to impacts while being inserted into the connector receptacle and may malfunction due to repeated attachment and detachment.

Therefore, there is an urgent need to develop an endoscope having a novel connector structure maintaining durability even through repeated attachment and detachment thereof.

In the case in which the endoscope receives power from an external source, abnormal power may be input due to a failure in the power-transmitting external device. When such abnormal power is directly transmitted to the bendable section, the bendable section may move differently from the intention of a user, i.e., a doctor, and in some cases, may injure a patient, i.e., a subject. Therefore, a safety device able to control the input of abnormal power into the endoscope is required.

The information disclosed in the Background section is technical information that the inventors possessed for, or acquired during, derivation of embodiments of the present disclosure and should not be taken as known technology disclosed to the public before the filing of the embodiments of the present disclosure.

DISCLOSURE

Technical Problem

Accordingly, the present disclosure has been made in consideration of the above-described problems occurring in the related art, and an aspect of the present disclosure provides an endoscope including a power receiving part having a novel structure able to efficiently receive power from an external source and store the same therein while maintaining control precision and stability.

The present disclosure also provides an endoscope further including a safety device configured to prevent abnormal power from being transmitted to a bendable section when the endoscope receives the abnormal power from an external source.

The present disclosure also provides an endoscope having a shock absorption structure able to withstand impacts caused by repeated attachment and detachment of the endoscope.

The objectives of the present disclosure are not limited to the aforementioned descriptions, and other objectives not explicitly disclosed herein will be clearly understood by a person having ordinary knowledge in the art from the description provided hereinafter.

Technical Solution

According to an aspect of the present disclosure, provided is an endoscope including a connector configured to be coupled to an external device and receive power from the external device.

The connector may include one or more:
a power transmission cable configured to transmit power to a bendable section;
a power receiving part including a first slider configured to move in a first direction by receiving power from the external device and a second slider configured to move in a second direction by receiving power from the external device like the first slider; and
a power transmission part configured to receive power from the power receiving part and transmit the same to the power transmission cable.

In some embodiments, the connector may include a housing accommodating the power receiving part and the power transmission part therein and a cover closing one end of the housing.

In some embodiments, the first slider may include a first coupling portion exposed externally of the cover and configured to receive power from the external device. In addition, the second slider may include a second coupling portion exposed externally of the cover and configured to receive power from the external device, like the first slider.

In some embodiments, the first coupling portion may have a shape corresponding to the shape of a first power providing portion providing power in the external device. In addition, the second coupling portion may have a shape corresponding to the shape of a second power providing portion providing power in the external device.

In some embodiments, the first slider may include a first slider body and a first coupling portion. In addition, the second slider may include a second slider body and a second coupling portion.

In some embodiments, the first coupling portion may include a first protrusion protruding from a first slider body. In addition, the second coupling portion may include a second protrusion protruding from a second slider body.

In some embodiments, the first slider and the second slider may be spaced apart from each other while being disposed in parallel.

In some embodiments, the first slider may reciprocate linearly in the first direction, and the second slider may reciprocate linearly in the second direction.

In some embodiments, the power receiving part may include a first sliding rail configured such that the first slider may move linearly in the first direction on the first sliding rail. In addition, the power receiving part may include a second sliding rail configured such that the second slider may move linearly in the second direction on the second sliding rail.

In some embodiments, the first sliding rail may include a first stoppers configured to restrain the movement of the first slider. In addition, the second sliding rail may include a second stopper configured to restrain the movement of the second slider.

In some embodiments, the first stoppers may be provided on both ends of the first sliding rail, respectively, and limit a range of upward and downward bending angles of the bendable section. In addition, the second stoppers may be provided on both ends of the second sliding rail, respectively, and limit a range of left and right bending angles of the bendable section.

In some embodiments, the first sliding rail and the second sliding rail of the power receiving part may be supported by a main frame of the power transmission part.

In some embodiments, the first sliding rail and the second sliding rail may include rear supports supporting the first slider and the second slider from behind, respectively, so that the first slider and the second slider are not pushed backwards when a user fits the connector into a connector receptacle of the external device.

In some embodiments, a rack gear may be provided on one side of each of the first slider and the second slider. The power transmission part may include: a pinion gear meshing with the rack gear, a sprocket connected to the pinion gear and configured to rotate together therewith, a power transmission chain meshing with the sprocket, and the power transmission cables connected to one side and the other side of the power transmission chain, respectively.

In some embodiments, the pinion gear and the sprocket may be integrated into a pinion-sprocket assembly. The pinion-sprocket assembly may be rotatably disposed on the main frame. In addition, the power transmission cables may be disposed on the main frame. The power transmission cables and the pinion-sprocket assembly may be disposed on the main frame to stably operate.

According to another aspect of the present disclosure, provided is an endoscope including a connector configured to be coupled to an external device and receive power from the external device.

The connector may include one or more among: a housing; a cover configured to face a connector receptacle of the external device when coupled to the external device and closing one end of the housing;
a cord protector having one side connected to a universal cord and the other side coupled to the other end of the housing and configured to protect a power transmission cable drawn out from the other end of the housing; and
a power receiving part and a power transmission part protected by the housing and the cover, wherein the power receiving part receives power from the external device and stores the same therein, and the power transmission part transmits power stored in the power receiving part to the power transmission cable.

Advantageous Effects

According to an embodiment of the present disclosure as described above, provided is the endoscope including the power receiving part having a novel structure able to efficiently receive power from an external source and store the same therein while maintaining control precision and stability In addition, the present disclosure has a variety of effects with excellent versatility depending on the embodiment, and such effects may be clearly understood from the following description of embodiments.

DESCRIPTION OF DRAWINGS

The following drawings accompanying the specification illustrate embodiments of the present disclosure and, together with the foregoing disclosure, serve to provide further understanding of the technical spirit of the present disclosure, and thus, the present disclosure should not be construed as being limited to the drawings.

MODE FOR INVENTION

Figure 1:
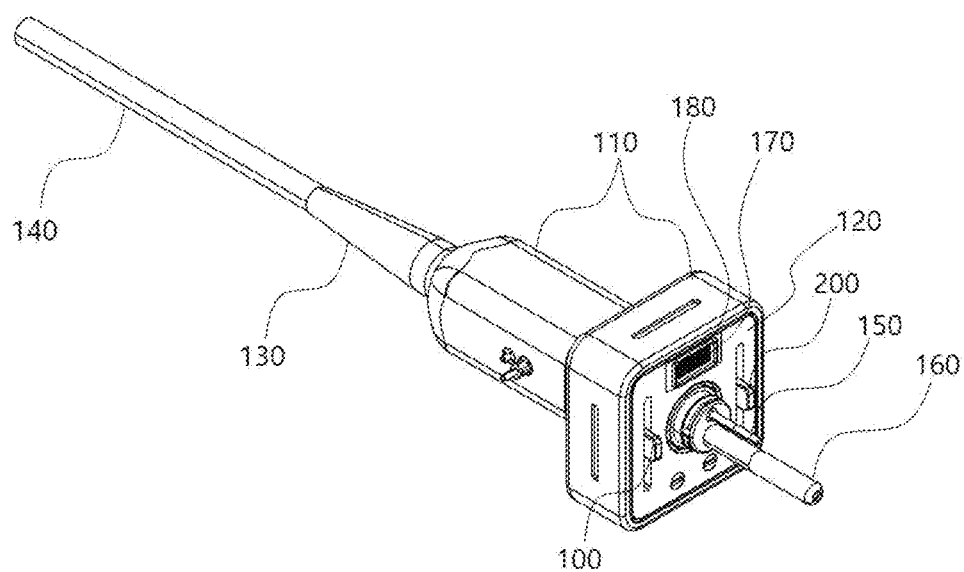
FIG. 1 illustrates an endoscope according to an embodiment of the present disclosure.

Advantages and features of the present disclosure, as well as methods of realizing the same, will be more clearly understood from the following detailed description of embodiments when taken in conjunction with the accompanying drawings. However, the present disclosure is not limited to specific embodiments to be described hereinafter but should be understood as including a variety of modifications, equivalents, and alternatives within the spirit and scope of the present disclosure. Rather, these embodiments are provided so that the description of the present disclosure will be complete and will fully convey the scope of the present disclosure to a person having ordinary skill in the art in the technical field to which the present disclosure pertains. In the following description of the present disclosure, a detailed description of related known technology will be omitted when the description may render the subject matter of the present disclosure unclear.

The terminology used in this application is used to describe specific embodiments only and is not intended to limit the invention. Expressions in the singular include the plural unless the context clearly indicates otherwise.

In the present application, the terms "includes" or "has" and the like are intended to designate the presence of the features, numbers, steps, actions, components, parts, or combinations thereof described in the specification, and are not intended to preclude the possibility of the presence or addition of one or more other features, numbers, steps, actions, components, parts, or combinations thereof. Terms such as first, second, and the like may be used to describe various components, but the components are not to be limited by such terms. Such terms are used only to distinguish one component from others.

Hereinafter, embodiments according to the present disclosure will be described in detail with reference to the accompanying drawings, wherein identical or corresponding components are given the same reference numerals and duplicate descriptions thereof are omitted.

In the specification, an external device may include a device separately present outside an endoscope. A connector of the endoscope may perform the function of connecting the endoscope to the external device. Here, the external device may include a power providing device. The power providing device may include, for example, a light source device, an image processing device, and the like.

The light source device described herein is merely an embodiment of the external device. In some embodiments, the external device is not limited to the light source device, and the light source device may be substituted by a separate device located outside the endoscope. In some embodiments, the light source device may be substituted with the power providing device.

Figure 2:
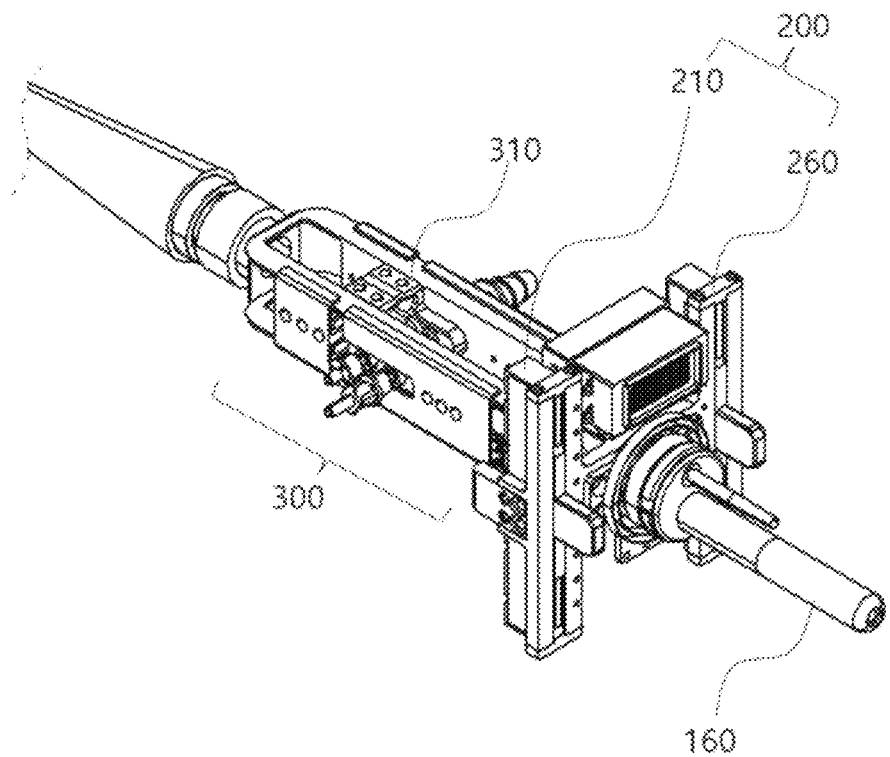
FIG. 2 schematically illustrates the shape of the endoscope of FIG. 1 from which the cover, the housing, and the cord protector are removed.

FIG. 1 illustrates an endoscope according to an embodiment of the present disclosure, and FIG. 2 schematically illustrates the shape of the endoscope of FIG. 1 from which a cover 120, a housing 110, and a cord protector 130 are removed.

The endoscope according to an embodiment of the present disclosure may include one or more among an insertion tube, a control body, a universal cord 140, and a connector 100.

In some embodiments, the control body may be disposed between one end of the insertion tube and one end of the universal cord 140, and the connector 100 may be connected to the other end of the universal cord 140.

The insertion tube may be a portion that is inserted into a patient's body when a user, i.e., a doctor, performs an endoscopy on the patient. The insertion tube 140 may include a tube tip, a bendable section, and a flexible portion.

The tube tip may be configured to illuminate a target area, collect image information, perform a treatment, or the like. The tube tip may be disposed on the distal end of the insertion tube, and may include an illumination means for illuminating the interior of the subject's body, an imaging means for imaging the interior of the subject's body, a biopsy channel for collecting tissue from the interior of the subject's body, an air-water channel for spraying air, water, or the like for various purposes, and the like.

The bendable section may perform a bending motion in response to the user's operation, and may be bent inside the body and travel along the interior of the curved tubular organ. The tube tip may be disposed on the distal end of the bendable section, and the distal end of the bendable section may bend in the bending motion to place the tube tip in a direction desired by the user.

The flexible portion may be disposed between the bendable section and the control body, and may be a portion that moves along with the bendable section when the bendable section travels through the gastrointestinal tract inside the patient's body.

The control body may be provided with a controller to control the bending motion of the bendable section, and may be provided with a flow control valve able to control a flow of air or water, or suction.

The insertion tube 140 may be connected to one side of the control body, and the universal cord 140 may be connected to the other side of the control body. The connector 100 may be connected to the distal end of the universal cord 140.

The universal cord 140 may connect the control body and the connector 100 to each other, and may serve to separate the connector 100 and the control body from each other so that a user can easily move when using the endoscope 100 by holding the control body 130. In some embodiments, the universal cord 140 may be omitted and the connector 100 may be connected to the other side of the control body.

In the specification, the light source device may include a light source generating light. Herein, the light source included in the light source device may include a light source such as a light-emitting diode (LED) according to embodiments, but any configuration able to generate light within the scope of technical concept may be included in the light source described herein.

The endoscope according to the present embodiment may receive light from the light source device and deliver the same to a lighting means. The lighting means of the endoscope according to the present embodiment receives light from the light source device and illuminates the interior of a subject's body, thereby allowing a user, i.e., a doctor, to examine the interior of the subject's body.

In the specification, the light source device may include a power source generating power. Power generated by the light source device according to the present embodiment may be power to be supplied to the endoscope according to the present embodiment.

The power source may refer to a motor in some embodiments, but any configuration able to generate power within the scope of technical concept may be included in the light source described herein.

The endoscope according to the present embodiment may receive power from the light source device and deliver the same to a bendable section. The bendable section of the endoscope according to the present embodiment may perform a bending motion by receiving power from the light source device so that a tube tip is directed toward a portion which is the target of the user, i.e., a doctor, inside the subject's body.

In some embodiments, the light source device may be provided with a connector receptacle. The connector receptacle may be a portion to which the connector 100 of the endoscope according to the present embodiment is mechanically and electrically coupled. This is similar to, for example, a process in which an electric plug is mechanically and electrically coupled to an electric socket.

The endoscope according to an embodiment of the present disclosure may include the connector 100 coupled to the light source device to be provided with power from the light source device. The connector 100 according to the present embodiment may be coupled and mechanically and electrically connected to the connector receptacle of the light source device.

The connector 100 of the endoscope according to the present embodiment may include one or more among the housing 110, the cover 120, the cord protector 130, a power receiving part 200, and a power transmission part 300.

In the connector 100 according to the present embodiment, the housing 110 may form the contour of the connector 100 and perform the function of protecting internal devices from the outside. The cover 120 may close one end of the housing 110 and, when the connector 100 is coupled to the light source device, may be disposed in a position facing the connector receptacle of the light source device. The cord protector 130 may perform the function of protecting various lines drawn out from the other end of the housing 110 and be connected to the universal cord 140.

The cover 120 of the connector 100 according to the present embodiment may have a structure by which one or more among a control signal terminal 170, an image signal terminal 180, an air tube coupling part 150, and a light guide coupling part 160 are exposed externally.

The connector receptacle of the light source device according to the present embodiment may be provided with a control signal receiver connected to the control signal terminal 170, an image signal receiver connected to the image signal terminal 180, an air nozzle connected to the air tube coupling part 150 and configured to spray air, and a light providing terminal connected to the light guide coupling part 160.

The control signal terminal 170 may transmit a power control command to the light source device, the image signal terminal 180 may transmit image information to the light source device, the air tube coupling part 150 may be provided with air from the light source device, and the light guide coupling part 160 may be provided with light from the light source device.

One or more among a control signal line connected to the control signal terminal 170, an image signal line connected to the image signal terminal 180, a light guide cable connected to the light guide coupling part 160, and an air tube connected to the air tube coupling part 150 may extend through the connector 100 according to the present embodiment. The cord protector 130 of the connector 100 according to the present embodiment may perform the function of protecting one or more among the control signal line, the image signal line, the light guide cable, and the air tube drawn out from the housing 110.

Figure 3:
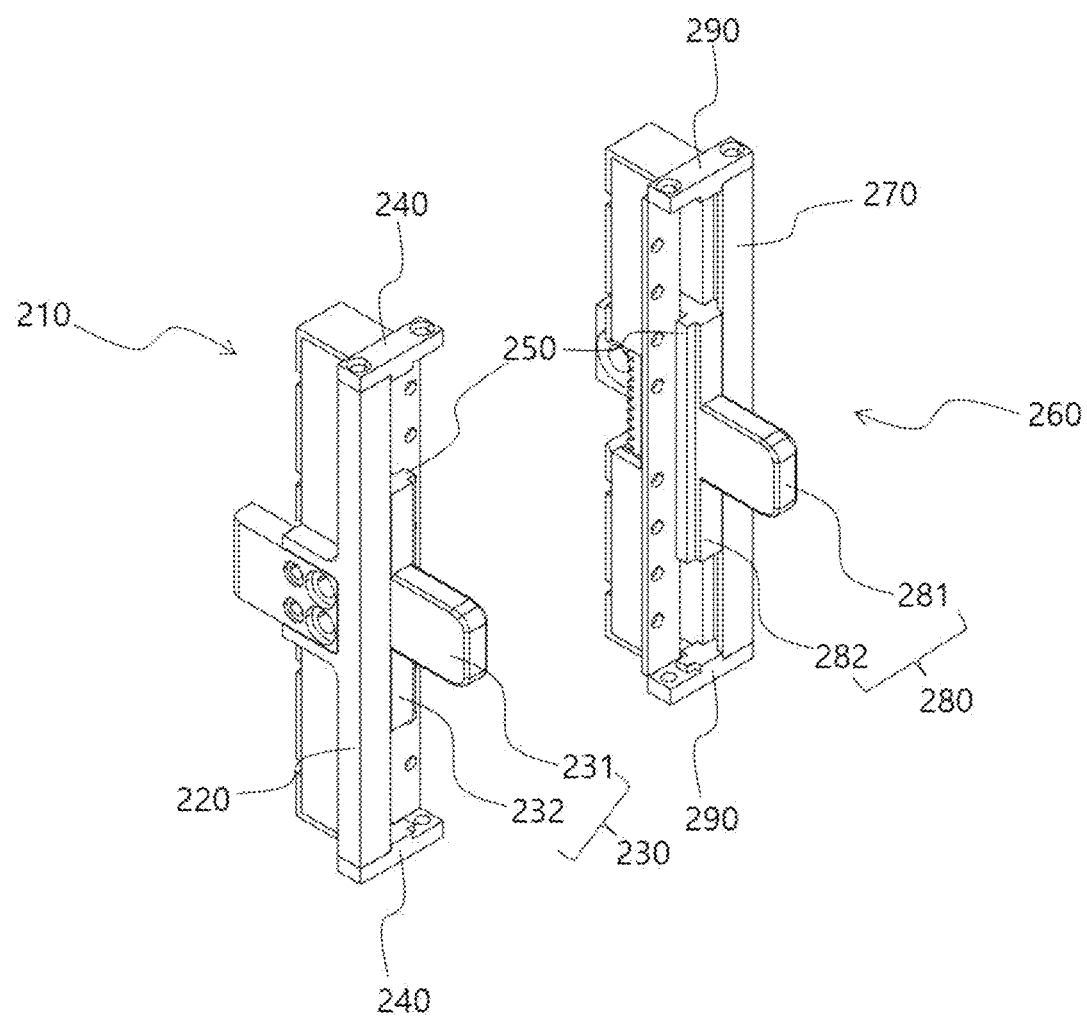
FIG. 3 schematically illustrates the configuration of the power receiving part according to an embodiment of the present disclosure.
Figure 4:
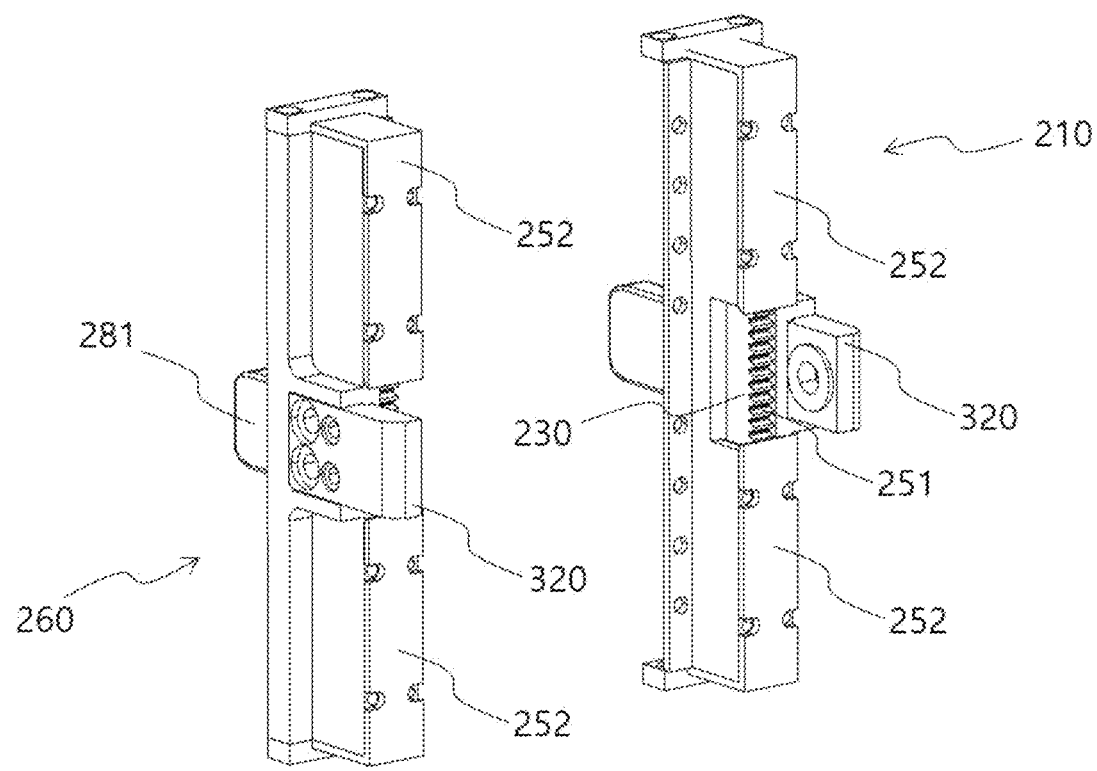
FIG. 4 illustrates the configuration of the power receiving part of FIG. 3 viewed at a different angle.

FIG. 3 schematically illustrates the configuration of the power receiving part 200 according to an embodiment of the present disclosure. FIG. 4 illustrates the configuration of the power receiving part 200 of FIG. 3 viewed at a different angle.

The connector 100 according to the present embodiment may include the power receiving part 200 and the power transmission part 300 described above. The power receiving part 200 may perform the function of receiving power from the light source device and accommodating the same. The power transmission part 300 may perform the function of transmitting power stored in the power receiving part 200 to power transmission cables 400.

In some embodiments, the power receiving part 200 may include a first slider 230 moving linearly in a first direction by receiving power from the light source device. The power receiving part 200 may also include a second slider 280 moving linearly in a second direction by receiving power from the light source device.

In some embodiments, the first slider 230 may be disposed on the connector 100 to reciprocate linearly in the first direction, and the second slider 280 may also be disposed on the connector 100 to reciprocate linearly in the second direction. In some embodiments, the first direction and the second direction may be in parallel to each other. In some embodiments, in the connector 100, the first slider 230 and the second slider 280 may be spaced apart from each other while being disposed in parallel.

In the endoscope according to the present disclosure, the structure for receiving power from the light source device by means of the first slider 230 and the second slider 280 of the connector 100 has a simple structure and thus may obtain durability in which no malfunction occurs even in the case that power is repeatedly received over an extended time and control stability and control precision may be advantageously improved.

In some embodiments, the first slider 230 may have a first coupling portion 231 exposed externally of the cover 120 and configured to receive power from the light source device. In addition, the second slider 280 may have a second coupling portion 281 exposed externally of the cover 120 and configured to receive power from the light source device.

The first coupling portion 231 may work in concert with a first power providing portion of the connector receptacle of the light source device and receive power provided by the first power providing portion to move the first slider 230. The second coupling portion 281 may work in concert with a second power providing portion of the connector receptacle of the light source device and receive power provided by the second power providing portion to move the second slider 280.

In some embodiments, the first coupling portion 231 may be formed to correspond to the shape of the first power providing portion which provides power in the light source device, while the second coupling portion 281 may be formed to correspond to the shape of the second power providing portion which provides power in the light source device.

The first coupling portion 231 and the first power providing portion may be variously expressed within the scope of technical concept in which the shapes thereof correspond to each other. The second coupling portion 281 and the second power providing portion may also be variously expressed within the scope of technical concept in which the shapes thereof correspond to each other.

In some embodiments, the first slider 230 may include a first slider body 232 and the first coupling portion 231, and the second slider 280 may include a second slider body 282 and the second coupling portion 281. In some embodiments, the first coupling portion 231 may include a first protrusion protruding from the first slider body 232, and the second coupling portion 281 may include a second protrusion protruding from the second slider body 282. The first protrusion may be a plurality of protrusions in some embodiments, and the second protrusion may be a plurality of protrusions in some embodiments.

The power receiving part 200 according to an embodiment of the present disclosure may have a first sliding rail 220 configured such that the first slider 230 may move linearly in the first direction on the first sliding rail 220. In addition, the power receiving part 200 may have a second sliding rail 270 configured such that the second slider 280 may move linearly in the second direction on the second sliding rail 270. In some embodiments, the first sliding rail 220 and the second sliding rail 270 may be spaced apart from each other while being disposed in parallel.

In some embodiments, the power receiving part 200 may be located on an inner surface of the cover 120 of the connector 100, and may include the first sliding rail 220 and the second sliding rail 270.

In some embodiments, the first sliding rail 220 may be provided with first stoppers 240 limiting the movement of the first slider 230, and the second sliding rail 270 may be provided with second stoppers 290 limiting the movement of the second slider 280.

In some embodiments, the first stoppers 240 may be provided on both ends of the first sliding rail 220, respectively, to limit the ranges of upward and downward bending angles of the bendable section. In addition, the second stoppers 290 may be provided on both ends of the second sliding rail 270, respectively, to limit the ranges of left and right bending angles of the bendable section.

That is, a pair of first stoppers 240 limiting the movement of the first slider 230 may be provided on both ends of the first sliding rail 220, respectively. Here, the pair of first stoppers 240 may limit the ranges of the angles of upward and downward bending movements of the bendable section.

In addition, a pair of second stoppers 290 limiting the movement of the second slider 280 may be provided on both ends of the second sliding rail 270, respectively. Here, the pair of second stoppers 290 may limit the ranges of the angles of left and right bending movements the bendable section.

In some embodiments, a fabricator may set the ranges of bending angles by means of the first stoppers 240 and the second stoppers 290. In some embodiments, the ranges of upward and downward bending angles of the bendable section may be set by a first distance between the pair of first stoppers 240, and the ranges of left and right bending angles of the bendable section may be set by a second distance between the pair of second stoppers 290.

The bendable section is required to perform a bending motion within predetermined ranges. This is because a patient is required to be protected since the bendable section moves inside a tubular organ of the patient's body and because the user, i.e., a doctor, is required to be able to estimate the bending angle.

In particular, when the bendable section bends by receiving power from a motor serving as a power source, the connector 100 may be excessively provided with power because, for example, a power supply configured to supply power to the motor may have a problem, the motor may malfunction, excessive current may suddenly flow through the motor, or the motor may operate abnormally for an unknown reason. Even in the case that power is excessively provided in this manner, the bendable section moving inside the patient's body is required to move within predetermined ranges of bending angles.

The configuration of the first stoppers 240 and the second stoppers 290 according to the present disclosure serves a safety device able to guarantee the safety of a patient by limiting the range of power reception of the power receiving part 200 so that the bending angles are allowed within predetermined ranges even in the case that the motor malfunctions.

In some embodiments, each of the first sliding rail 220 and the second sliding rail 270 of the power receiving part 200 may include rear supports 252 configured to support the first slider 230 and the second slider 280 from behind so that neither the first slider 230 nor the second slider 280 is pushed backwards when the user fits the connector 100 into the connector receptacle of the light source device.

The first slider 230 and the first sliding rail 220 may have a rail structure 250 on which the first slider 230 may move within the first sliding rail 220. A protrusion configured to receive power from the light source device may be provided on the front surface of the first slider 230, and a rack gear 251 configured to transmit power to the power transmission part 300 may be provided on the rear surface of the first slider 230.

The first stoppers 240 configured to stop the first slider 230 moving in the first direction so as not to move further may be provided on both ends of the first sliding rail 220, and the rear supports 252 may be provided on the rear surface of the first sliding rail 220 so as to withstand impacts when the first protrusion of the first slider 230 is coupled to the first power providing portion provided in the connector receptacle of the light source device.

In some embodiments, the first stoppers 240 and the rear supports 252 may be formed integrally. In some embodiments, each of the first stoppers 240 and a corresponding one of the rear supports 252 may be an L-shaped bracket.

The rail structure 250 formed by the first slider 230 and the first sliding rail 220 may be designed to have a predetermined gap. Thus, in a process in which the user couples the connector 100 to the connector receptacle of the light source device, the first slider 230 is pushed backwards through the gap of the rail structure 250 before the backward movement thereof is stopped at a predetermined position by contact with the rear supports 252. That is, the first slider 230 is supported by the rear supports 252 and thus is not pushed further backwards.

When the user couples the connector 100 of the endoscope to the connector receptacle of the light source device, the connector 100 and the connector receptacle are brought into contact with each other, thereby leading to a physical collision between the two components. The user may habitually strongly push the connector 100 toward the connector receptacle while being concerned about poor electrical contact between the connector 100 and the connector receptacle, and as a reaction, the connector receptacle may also strongly push the connector 100.

Thus, when the connector 100 is coupled, the first slider 230 is strongly pushed backwards. The first slider 230 is coupled to the first sliding rail 220 by means of the rail structure 250 and thus may withstand a predetermined degree of impact, but the rail structure 250 alone may not withstand fatigue due to repetitive attachment and detachment.

Due to the fatigue caused by the repetitive attachment and detachment of the connector 100, the rail structure 250 of the first slider 230 and the first sliding rail 220 may be resultantly deformed so as to malfunction or be broken.

In the present disclosure, since the first sliding rail 220 has the configuration of the rear supports 252 restraining the backward movement of the first slider 230, even in the case that the user strongly pushes and fits the connector 100 into connector receptacle, the rear supports 252 restrain the backward movement of the first slider 230 to protect the rail structure 250 which the first slider 230 and the first sliding rail 220 have, thereby improving the durability of the endoscope.

The foregoing description is only about the first slider 230 and the first sliding rail 220, the same functions and effects as those of the rear supports 252 and the stoppers described above may be applied to the second slider 280 and the second sliding rail 270.

The power transmission part 300 according to an embodiment of the present disclosure will be described.

Figure 5:
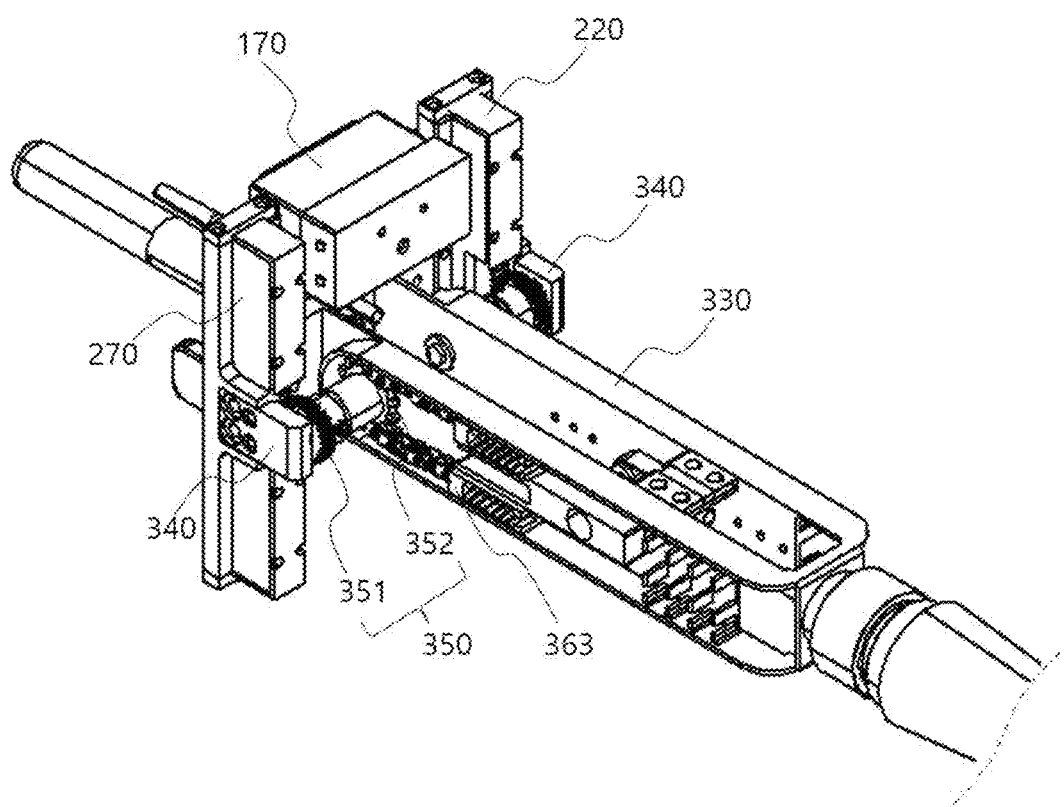
FIG. 5 illustrates the shape of the power receiving part and the power transmission part.
Figure 6:
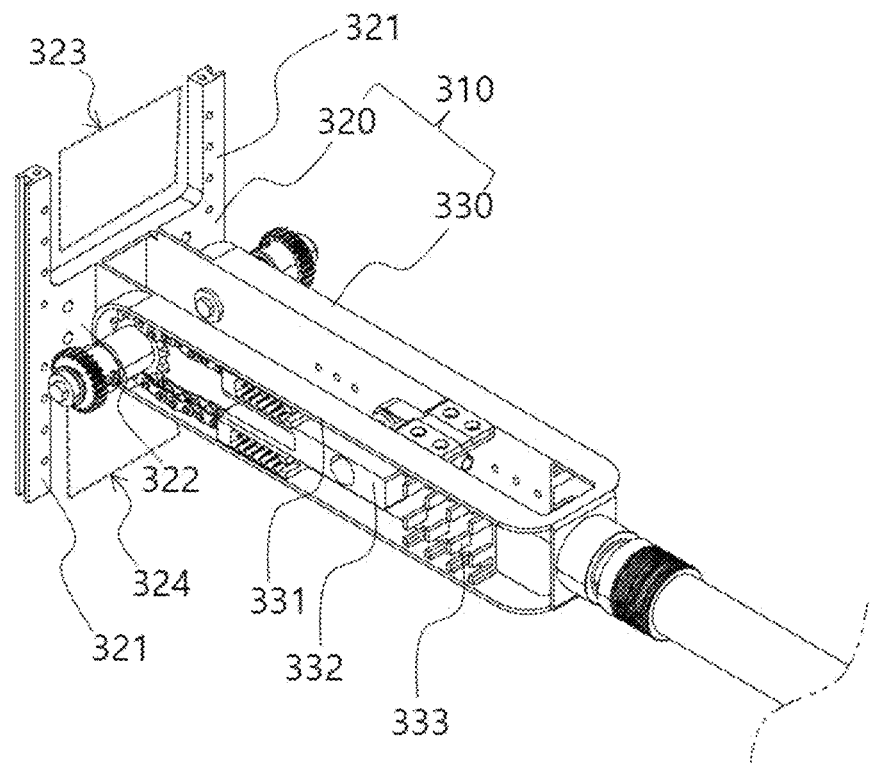
FIG. 6 illustrates the shape of the power transmission part in which a portion of the power receiving part is removed.

FIG. 5 illustrates the shape of the power receiving part and the power transmission part, and FIG. 6 illustrates the shape of the power transmission part in which a portion of the power receiving part is removed.

Figure 7:
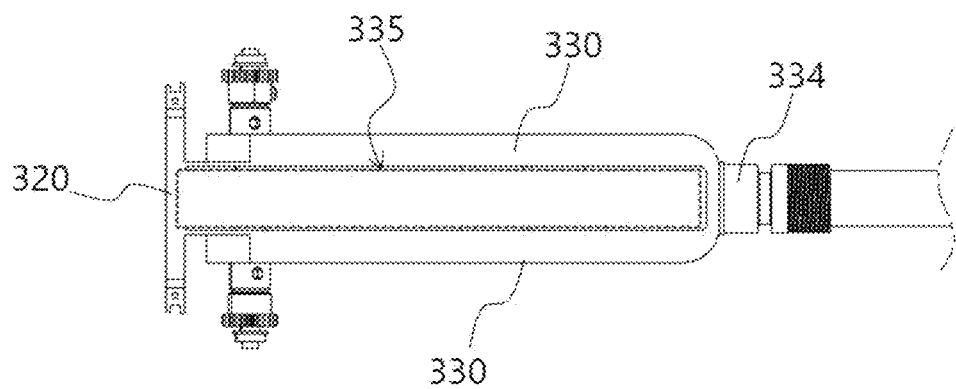
FIG. 7 illustrates the shape of the main frame according to an embodiment of the present disclosure.
Figure 8:
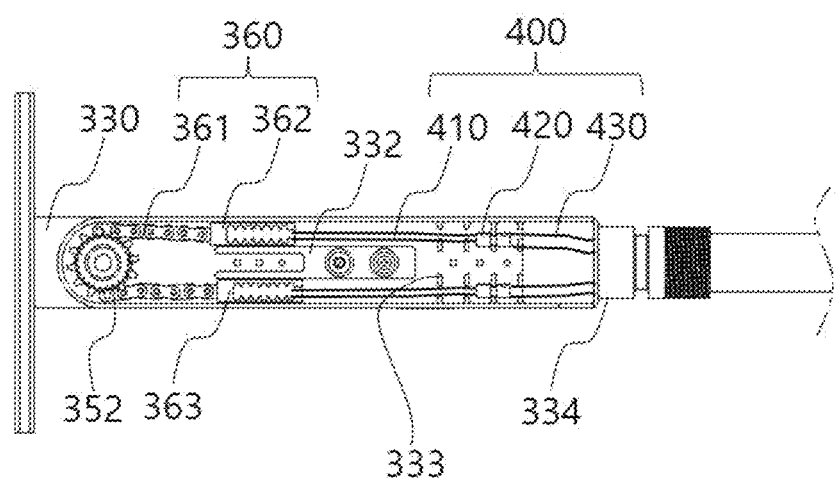
FIG. 8 illustrates the shape in which the configuration of the power transmission part and the power transmission cables are connected according to an embodiment of the present disclosure.

FIG. 7 illustrates the shape of a main frame according to an embodiment of the present disclosure, and FIG. 8 illustrates the shape in which the configuration of the power transmission part and the power transmission cables are connected according to an embodiment of the present disclosure.

When the power receiving part 200 receives power from the light source device, the power transmission part 300 may receive power from the power receiving part 200 and transmit the same to the power transmission cables 400.

In some embodiments, the power transmission part 300 may include a main frame 310. The first sliding rail 220 and the second sliding rail 270 of the power receiving part 200 may be supported by the main frame 310 of the power transmission part 300.

Specifically, the power transmission part 300 according to the present embodiment may include at least one of the main frame 310, a rotating structure 350, a power transmission chain 361, and the power transmission cables 400. Here, the rotating structure 350 may have a configuration to which a pinion gear 351 and a sprocket 352 are coupled.

In some embodiments, the rack gear 251 may be provided on one side of each of the first slider 230 and the second slider 280. Here, the rack gear 251 may mesh with the pinion gear 351, and the sprocket 352 may mesh with the power transmission chain 361.

The power transmission part 300 and the power receiving part 200 may be separate configurations. In some embodiments, the power transmission part 300 and the power receiving part 200 may be formed integrally.

A process in which power is transmitted from the power receiving part 200 to the power transmission part 300 according to the present embodiment will be described. The first coupling portion 231 or the second coupling portion 281 of the power receiving part 200 receives power provided by the light source device. Then, the first slider 230 or second slider 280 moves linearly through receiving the power. Each of the first slider 230 and the second slider 280 transmits rotational force to the pinion gear 351 by means of the rack gear 251 provided on one side. Then, the pinion gear 351 transmits the rotational force to the sprocket 352. When the sprocket 352 transmits the power to the power transmission chain 361, the power transmission chain 361 transmits the power to the power transmission cables 400.

Here, the power transmission cables 400 disposed on both ends of the power transmission chain 361 are two power transmission cables. The power transmission cables 400 are configured such that when one of the two power transmission cables 400 is pulled, the other power transmission cable 400 is pushed. Thus, the pair of power transmission cables 400 perform the bending motion of the bendable section by being pulled or pushed while being paired.

Another aspect of the endoscope according to the present disclosure will be described. The endoscope according to the present embodiment is substantially the same technical concept as the foregoing endoscope, except for the expressions used in the disclosure thereof.

The endoscope according to an embodiment of the present disclosure may have a connector 100 coupled to the light source device to receive power from the light source device.

The connector 100 of the endoscope according to the present embodiment may include one or more among: a power receiving part 200 including a slider moving by receiving power from the light source device and a sliding rail on which the slider moves; a main frame 310 supporting the power receiving part 200; power transmission cables 400 disposed on one side of the main frame 310 to transmit power to the bendable section;

a rotating structure 350 rotatably coupled to the main frame 310 to receive rotational force in response to the movement of the slider; and a chain-slider assembly 360 working in concert with the rotating structure 350 to transmit power to the power transmission cables 400.

In some embodiments, the main frame 310 may include a vertical frame 320 and horizontal frames 330. The power receiving part 200 may be supported on the vertical frame 320, and the rotating structure 350 and the chain-slider assembly 360 may be disposed on the horizontal frames 330.

In some embodiments, the power receiving part 200 may include a first power receiving part 210 and a second power receiving part 260. The vertical frame 320 may support the first power receiving part 210 and the second power receiving part 260 by spacing the first power receiving part 210 and the second power receiving part 260 apart from each other by a predetermined distance.

In some embodiments, the horizontal frames 330 may include a pair of a first horizontal frame 330 and a second horizontal frame 330 disposed in parallel to each other.

A light guide cable delivering light provided by the light source device to the tube tip may be disposed to extend through a through-hole formed in a bridge 322 between the first power receiving part 210 and the second power receiving part 260 and a central space 335 formed between the first horizontal frame 330 and the second horizontal frame 330. As the predetermined space is formed within the main frame 310 according to the present disclosure in this manner, a variety of lines, such as a light guide cable and an air tube, may extend through the space and thus components may be efficiently disposed within the connector 100. Accordingly, the connector 100 may be advantageously fabricated to be compact.

In some embodiments, the vertical frame 320 may include a first connecting portion 321 to which the first power receiving part 210 is connected, a second connecting portion 321 to which the second power receiving part 260 is connected, and the bridge 322 connecting the first connecting portion 321 and the second connecting portion 321 to each other. In some embodiments, the power receiving part 200 and the vertical frame 320 may be formed integrally, and the first power receiving part 210, the second power receiving part 260, and the bridge 322 may be provided in the shape of the letter "H."

When the connector 100 faces the connector receptacle of the light source device, the vertical frame 320 may be disposed at an angle at which the vertical frame 320 faces the connector receptacle, together with the connector 100.

In the present embodiment, the slider has substantially the same configuration as the first slider 230 and the second slider 280 of the foregoing embodiment. In addition, the sliding rail has substantially the same configuration as the first sliding rail 220 and the second sliding rail 270 described above. In addition, the first power receiving part 210 may include the first slider 230 and the first sliding rail 220, and the second power receiving part 260 may include the second slider 280 and the second sliding rail 270.

In some embodiments, the rotating structure 350 may include a configuration to which the pinion gear 351 and the sprocket 352 are coupled.

One or more among the control signal terminal 170, the light guide coupling part 160, the air tube coupling part 150, the image signal terminal 180, the first power receiving part 210, and the second power receiving part 260 may be exposed on the outer surface of the cover 120 of the connector 100 according to the present embodiment.

The vertical frame 320 may be disposed within the cover 120 to face the cover 120. Here, both the control signal terminal 170 and the image signal terminal 180 may be disposed in a first space 323 or a second space 324, three sides of which are formed by the first power receiving part 210, the second power receiving part 260, and the bridge 322. In addition, in some embodiments, the control signal terminal 170 may be disposed in the first space 323, and the image signal terminal 180 may be disposed in the second space 324. In addition, in some embodiments, the control signal terminal 170 may be disposed in the second space 324, and the image signal terminal 180 may be disposed in the first space 323.

That is, the control signal terminal 170 or the image signal terminal 180 may be combined and disposed in a single place or may be disposed separately.

Referring to FIG. 1, the lines may be disposed in a structure in which both the control signal terminal 170 and the image signal terminal 180 are located in the first space 323 formed in the top end of the bridge 322 in the letter "H" shape, such that that the connection of the power receiving part 200 and the vertical frame 320 is exposed and the light guide coupling part 160 and the air tube coupling part 150 are located in the through-hole formed in the bridge 322.

The horizontal frames 330 may extend on the rear surface of the vertical frame 320. The horizontal frames 330 may be a pair of frames including the first horizontal frame 330 and the second horizontal frame 330. A ring portion 334 having the shape of a ring may be provided on the rear end of each of the first horizontal frame 330 and the second horizontal frame 330.

One or more among the control signal line connected to the control signal terminal 170, the image signal line connected to the image signal terminal 180, the light guide cable, the air tube, and the power transmission cables 400 may be drawn out from the connector 100 through the ring portion 334 and extend to the universal cord 140 and the control body.

In some embodiments, the chain-slider assembly 360 may include the power transmission chain 361, a top slider 362, and a bottom slider 363. The chain-slider assembly 360 may have a structure in which the top slider 362 and the bottom slider 363 are coupled to both ends of the power transmission chain 361, respectively.

In some embodiments, a horizontal sliding rail portion 332 may be provided on the horizontal frames 330, and the top slider 362 and the bottom slider 363 may reciprocate linearly on the horizontal sliding rail portion 332 in a stable manner.

The top slider 362 and the bottom slider 363 may be connected to the power transmission cables 400, respectively. The power transmission chain 361 meshed with the sprocket 352 may move in response to the rotation of the sprocket 352, and the top slider 362 and the bottom slider 363 coupled to both ends of the power transmission chain 361 may move linearly in opposite directions by means of the power transmission chain 361, thereby pushing or pulling the power transmission cables 400.

Since the power transmission cables 400 are coupled to the top slider 362 and the bottom slider 363, respectively, power may be transmitted to the bendable section in such a manner that when one of the paired power transmission cables 400 is pulled, the other power transmission cable 400 is pushed.

In some embodiments, a shaft holding part 340 may be provided at the rear of the sliding rails. The rotating structure 350 is rotatable with one side thereof being disposed on the shaft holding part 340 and the other side thereof being disposed on the horizontal frames 330.

In some embodiments, in the rotating structure 350, the sprocket 352 may be disposed adjacent to the horizontal frames 330 and the pinion gear 351 may be disposed outside the sprocket 352. In this case, a guide 331 may protrude from the main frame 310, i.e., the horizontal frames 330, to protect the sprocket 352 and the power transmission chain 361, thereby protecting the rotating structure 350 and the chain-slider assembly 360.

In the present embodiment, the power transmission cables 400 may perform the function of transmitting power received from the power transmission part of the connector to the bendable section. The configuration of each of the power transmission cables 400 according to the present embodiment may include a mechanical cord 410, a cord protection pipe 430, and a holder 420.

Each of the power transmission cables 400 has a structure in which the mechanical cord 410 may be inserted into the cord protection pipe 430 to slide within the cord protection pipe 430. The power transmission cables 400 may be provided a pair of two power transmission cables. That is, in some embodiments, the number of the power transmission cables 400 may be at least 4. A pair of mechanical cords 410 may move with one of the paired mechanical cords 410 coupled to the top slider and the other of the paired mechanical cords 410 coupled to the bottom slider. The cord protection pipe 430 may perform the function of protecting the mechanical cords. A plurality of lines are disposed in a complicated arrangement inside the connector, the universal cord control body, the insertion tube, or the like. Thus, when the universal cord or the insertion tube is entangled, the lines therein may be entangled, thereby causing the endoscope to malfunction. The mechanical cords 410 allow the power transmission cables 400 according to the present embodiment to move within the cord protection pipe 430 using the configuration of the cord protection pipe 430, thereby fundamentally preventing the cord from being entangled.

In each of the power transmission cables 400, the holder 420 may be connected to the distal end of the cord protection pipe 430 and held by a holding pin part 333 protruding from the horizontal frame. The holding pin part 333 includes a plurality of pins. A fabricator may receive power by disposing the holders 420 on the holding pin parts 333 and coupling the mechanical cords 410 drawn from the cord protection pipes 430 and the holders 420 to the top slider and the bottom slider, respectively. Each of the cord protection pipes 430 is configured such that the diameter thereof decreases when stretched. Accordingly, the fabricator may set the length of the cord protection pipe 430 and provide a predetermined degree of friction to the mechanical cord 410 by fixing the holder 420 to an intended position of the holding pin part 333.

In the specification of the present disclosure, the use of the term "the or said" and similar denoting terms may correspond to both singular and plural forms. Furthermore, recitation of ranges of values herein are merely intended to refer to respective separate values falling within the respective ranges and, unless otherwise indicated herein, the respective separate values are incorporated herein as if individually recited herein.

Finally, the operations of any method described herein may be performed in any suitable order unless otherwise indicated herein or otherwise clearly contradicted by the context. However, the operations shall not be limited to the described sequence. The use of any examples or exemplary languages (e.g., "such as") provided herein, is intended merely to better illustrate the present disclosure and does not pose a limitation on the scope of the present disclosure unless otherwise defined by the Claims. In addition, a person having ordinary knowledge in the art will appreciate that various modifications, combinations, and changes are possible according to design conditions and factors within the scope of the Claims or equivalents thereof.

Therefore, the spirit of the present disclosure shall not be limited to the above-described embodiments, and the entire scope of the appended claims and equivalents thereof will fall within the scope and spirit of the present disclosure.

DESCRIPTION OF REFERENCE NUMERALS OF DRAWINGS

100: connector
110: housing
120: cover
130: cord protector
140: universal cord
150: air tube coupling part
160: light guide coupling part
170: control signal terminal
180: image signal terminal
200: power receiving part
210: first power receiving part
220: first sliding rail
230: first slider
231: first coupling portion
232: first slider body
240: first stopper
250: rail structure
251: rack gear
252: rear support
260: second power receiving part
270: second sliding rail
280: second slider
281: second coupling portion
282: second slider body
290: second stopper
300: power transmission part
310: main frame
320: vertical frame
321: connecting portion
322: bridge
323: first space
324: second space
330: horizontal frame
331: guide
332: horizontal sliding rail portion
333: holding pin part
334: ring portion
335: central space
340: shaft holding part
350: rotating structure
351: pinion gear
352: sprocket
360: chain-slider assembly
361: power transmission chain
362: top slider
363: bottom slider
400: power transmission cable
410: mechanical cord
420: holder
430: cord protection pipe

The invention claimed is:

1. An endoscope comprising:
a connector configured to be coupled to an external device and receive power from the external device,
wherein the connector comprises:
a power transmission cable configured to transmit power to a bendable section;
a power receiving part comprising a first slider configured to move in a first direction by receiving power from the external device and a second slider configured to move in a second direction by receiving power from the external device; and
a power transmission part configured to receive power from the power receiving part and transmit the same to the power transmission cable.

2. The endoscope of claim 1, wherein the connector comprises a cover and a housing accommodating the power receiving part and the power transmission part therein, and the cover closes one end of the housing, and
wherein the first slider comprises a first coupling portion exposed externally of the cover and configured to receive power from the external device and the second slider comprises a second coupling portion exposed externally of the cover and configured to receive power from the external device.

3. The endoscope of claim 2, wherein the first coupling portion comprises a first protrusion protruding from a first slider body, and the second coupling portion comprises a second protrusion protruding from a second slider body.

4. The endoscope of claim 1, wherein the first slider and the second slider are spaced apart from each other.

5. The endoscope of claim 1, wherein the power receiving part comprises a first sliding rail configured such that the first slider moves linearly in the first direction on the first sliding rail and a second sliding rail configured such that the second slider moves linearly in the second direction on the second sliding rail.

6. The endoscope of claim 5, wherein the first sliding rail and the second sliding rail of the power receiving part are supported by a main frame of the power transmission part.

7. The endoscope of claim 5, wherein the first sliding rail and the second sliding rail comprise rear supports supporting the first slider and the second slider, respectively.

8. The endoscope of claim 1, wherein two respective rack gears are provided on one side of each of the first slider and the second slider, and the power transmission part comprises:
a pinion gear meshing with the rack gear;
a sprocket connected to the pinion gear and configured to rotate together therewith;
a power transmission chain meshing with the sprocket; and
the power transmission cables connected to one side and the other side of the power transmission chain, respectively.

\* \* \* \* \*